United States Patent [19]

Mark et al.

[11] 4,394,324

[45] Jul. 19, 1983

[54] STABLE ANTIMONY ORGANOPHOSPHORODITHIOATES

[75] Inventors: Harold W. Mark; Brent J. Bertus; John S. Roberts, all of Bartlesville, Okla.

[73] Assignee: Phillips Petroleum Company, Bartlesville, Okla.

[21] Appl. No.: 264,526

[22] Filed: May 18, 1981

[51] Int. Cl.³ ............................................... C07F 9/90
[52] U.S. Cl. .................................. 260/446; 252/437; 208/113
[58] Field of Search ......................... 260/446; 252/437

[56] References Cited

U.S. PATENT DOCUMENTS

| | | | |
|---|---|---|---|
| 2,862,947 | 12/1958 | Goldsmith | 260/461 |
| 3,396,183 | 8/1968 | Brasch | 260/429 |
| 3,426,054 | 2/1969 | Schneider et al. | 260/429.9 |
| 3,573,293 | 3/1971 | Wiese | 260/242 |
| 4,025,458 | 5/1977 | McKay | 260/446 X |
| 4,031,002 | 6/1977 | McKay | 208/113 |
| 4,166,806 | 9/1979 | McKay | 242/437 |
| 4,167,471 | 9/1979 | Bertus et al. | 260/446 X |
| 4,207,204 | 6/1980 | McKay et al. | 260/446 X |

Primary Examiner—Helen M. S. Sneed

[57] ABSTRACT

Antimony passivators for cracking catalysts are rendered more stable by employing excess alcohol during their preparation.

9 Claims, No Drawings

STABLE ANTIMONY ORGANOPHOSPHORODITHIOATES

BACKGROUND OF THE INVENTION

The use of certain antimony-containing agents in metals-passivating cracking catalysts is sometimes hindered by the presence therein of impurities. The impurities comprise substances found in the antimony products, such as by-products, unreacted reagents, and decomposition products. Significant expenditures of time, energy, and money are often required to remove them.

THE INVENTION

It has been discovered that antimony diorganophosphorodithioates can be produced in a highly pure and, therefore, highly stable form by employing excess alcohol during the preparation of the diorganophosphorodithioic acid intermediate.

In one embodiment, hydrocarbyl phosphorodithioic acid is formed by combining $P_2S_5$ in a hydrocarbon diluent with a 5 mole % excess of a hydrocarbyl alcohol, such as 1-propanol. The resultant acid solution is treated with $Sb_2O_3$ to form the antimony dipropyl phosphorodithioate product. The product is stable due to the substantial absence of undesirable by-products or decomposition products.

OBJECTS OF THE INVENTION

It is one object of the invention to improve the efficiency with which stable antimony organophosphorodithioates are produced.

It is another object of the invention to employ a process by which certain antimony salts can be more economically produced.

It is another object of the invention to provide a group of passivation agents which need not be purified prior to use.

It is still another object to provide a process by which a metals passivation catalyst can be internally stabilized.

DESCRIPTION OF THE INVENTION

The antimony salts produced in accordance with the invention conform to the general formula

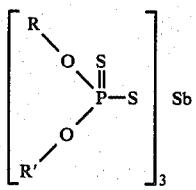

wherein R and R' can be the same or different and are hydrocarbyl radicals containing from 1 to 18 carbon atoms.

The R and R' moieties are derived from hydroxyl components such as mono-, and polyhydroxy-substituted hydrocarbons. Preferably, R and R' are derived from monohydroxy-substituted compounds containing 1 to 12 carbon atoms. Useful compounds include aromatic, cycloaliphatic, aliphatic, and branched-chain alcohols. Phenol, methylcyclohexanol, n-decanol, n-propanol, and isopropanol are useful.

The antimony salts can be called "antimony dihydrocarbylphosphorodithioates", "antimony tris-(O,O-dihydrocarbylphosphorodithioates", and "antimony dihydrocarbyldithiophosphates".

The salts are produced via a two-step process. In the first step, the hydroxy component reacts with the phosphorus and sulfur component to yield an acid intermediate. In the second step, an antimony-containing compound reacts with the acid intermediate to yield the desired antimony dihydrocarbylphosphorodithioate.

The hydroxyl component, which can contain one or several hydroxy-substituted hydrocarbons, has been described above.

The phosphorus and sulfur component employed in the first step can be one or more substances which contain both phosphorus and sulfur and in which phosphorus has a valence of 1 to 5, and sulfur has a valence of 2 to 6. Molecules in which either or both have fractional valences are operable. Useful compounds include: phosphorus disulfide ($PS_2$, $P_3S_6$), diphosphorus trisulfide ($P_2S_3$, $P_4S_6$), and diphosphorus pentasulfide ($P_2S_5$, $P_4S_{10}$). $P_2S_5$ is preferred.

It has been found that significant improvements in the stability of antimony hydrocarbylphosphorodithioates are achieved via the use, in the acid-forming step, of an excess of the hydroxyl reactant. The excess employed is small, but it is sufficient to aid in the formation of a stable antimony product in the subsequent salt-forming step. The use of a minor but effective amount of the hydroxyl component results in antimony salts containing fewer impurities, such as by-products, unreacted reagents, and decomposition products, e.g., hydrogen sulfide. Generally, excesses of up to 100% can be employed, with excess of about 1 to 20% molar excesses being the norm. Preferably, molar excesses of about 3 to 10% will be used.

The reaction between the hydroxyl-containing component and the phosphorus and sulfur component is preferably carried out in the presence of an inert diluent. The diluent is generally a hydrocarbon liquid. Useful diluents include hexane, heptane, octane, dodecane, gasoline, kerosene, mineral oil, cyclohexane, benzene, toluene, and xylene. The diluent is used in a concentration such that for every part by weight of antimony dihydrocarbylphosphorodithioate to be produced, there will be 0.1 to 10 parts by weight of diluent present.

It is preferred that the reaction between the hydroxy component and the phosphorus and sulfur component be conducted in an apparatus which permits temperature control and the elimination of undesired by-products. Normally, reaction temperature will range from 0° to 100° C., with 20° to 60° C. preferred.

While reaction times can vary, the reaction is generally conducted within time limits which conform to safety as well as economic considerations. Reaction times of about ½ hour to about 100 hours are normal. Preferably, the reaction takes place in 1 to 3 hours.

The product formed in this initial reaction will contain one or more hydrocarbylphosphorodithioic acid intermediates. These intermediates are reacted with antimony compounds to yield the desired salts.

In one embodiment, the invention can be characterized as a "one-pot" process. That is, when the acid production is substantially complete, the reaction of the acid and the antimony compound can be conducted in the same location or vessel in which the acid intermediate was formed. This eliminates the need for filtration or other purification of the intermediate.

The antimony compounds employed in the salt-forming reaction conform to the formula $Sb_mX_n$, wherein X includes —O, —OH, —OOCR", —Cl, —Br, or —F; R" is a $C_{1-12}$ organic radical; m is 1 or 2; and n is 1 to 5. Useful compounds include the oxides and hydroxides of antimony, antimony acetate, and the chlorides of antimony. Antimony oxides and hydroxides are preferred.

The antimony compound is reacted with the acid intermediate at a molar antimony to acid ratio of about 1:5 to 1:2, with 1:3 preferred. A slight excess of either component may be used in order to shift the chemical equilibrium in favor of the salt product.

The antimony compound can be added to the intermediate by itself or in admixture with an inert carrier. For example, if antimony oxide is employed, it can be added in its dry form or in a slurry with a hydrocarbon diluent.

While the temperature at which the reaction takes place is any temperature at which the salt formation takes place, normally temperatures will lie between 0° and 110° C., with 40° to 90° C. preferred.

The salt-forming reaction can be characterized as a condensation reaction. Accordingly, water or other condensation by-products are produced along with the antimony hydrocarbylphosphorodithioates. These by-products can be removed via conventional techniques, such as azeotropic distillation or vacuum distillation. Condensation by-products can be removed during or after the condensation step.

The antimony dihydrocarbylphosphorodithioates produced in accordance with the invention are stable materials requiring minimal treatment for handling and storage.

Among their uses are the passivation of metal contaminants produced during the catalytic cracking of hydrocarbons and hydrocarbon mixtures. U.S. Pat. Nos. 4,031,002 and 4,166,806 describe their use in cracking operations. The disclosures of these patents are incorporated herein by reference.

EXAMPLES

EXAMPLE I

Preparation of antimony tris-O,O-di-n-propyl phosphorodithioate using 5% molar excess 1-propanol In an 0.5 L flask fitted with a heating mantle, a slurry of 60.0 g (0.27 mol) $P_2S_5$ in 36.4 g kerosene was combined with 68.14 g (1.134 mol, 5% excess) $1-C_3H_7OH$. The temperature of the stirred mixture rose to about 55° C. as $H_2S$ evolved. After $H_2S$ evolution ceased the temperature was maintained at 55° C. by heating for ½ hour. The green colored mixture was allowed to cool to 40° C. This completed the first step, formation of di-n-propyl phosphorodithioic acid.

Then 23.6 g (0.81 mol) $Sb_2O_3$ was added to the above reaction mixture. The temperature rose to 80° C. as the mixture turned a yellow color. The temperature was maintained at 55° C. with heating while vacuum from a water aspirator was applied and nitrogen purged the system to remove by-product water.

The product was filtered through #2 Whatman paper to remove a slight amount of orange-red solid (less than 0.1 g). No more of this solid formed on storage. The product was a clear yellow liquid.

EXAMPLE II

Preparation of tris-O,O-di-n-propyl phosphorodithioate using stoichiometric quantities of $P_2S_5$ and 1-propanol In a concurrent run using the same size apparatus as in Example I, a slurry of 60.0 g (0.270 mol) of $P_2S_5$ in 36.4 g kerosene was combined with 64.9 g (1.08 mol, stoichiometric amount) $1-C_3H_7OH$. The remainder of this preparation was carried out in the same manner and with the same amount of $Sb_2O_3$ as in Example I the only differences in the results were that the reaction mixture turned yellow-orange rather than yellow (as in Example I) upon reaction of the $Sb_2O_3$ and upon filtration 1–2 g orange solid was removed. This undesirable solid may continue to form when the yellow liquid product is stored and tends to clog filters or pumps in subsequent use.

Reasonable variations, such as would occur to a skilled artisan, are within the scope of the invention.

We claim:

1. Stabilized antimony hydrocarbylphosphorodithioate salts produced by the steps of:
   (1) reacting a molar excess of a hydroxyl component with one or more substances containing phosphorus and sulfur, and
   (2) reacting the product of step (1) with an antimony-containing compound.

2. The salts of claim 1 wherein the reactants are selected from $C_{1-12}$, monoalcohols, phosphorus sulfides, and antimony oxides or hydroxides.

3. The salts of claim 1 wherein the reactants are n-propyl alcohol, diphosphorus pentasulfide, and antimony oxide.

4. A process of producing stabilized antimony salts of hydrocarbylphorodithioic acid comprising:
   (1) reacting a molar excess of at least one alcohol with at least one substance containing phosphorus and sulfur, to produce an acid intermediate, and
   (2) reacting the intermediate formed in step (1) with an antimony-containing compound.

5. The process of claim 4 wherein step (2) is a condensation reaction.

6. The process of claim 5 wherein water is removed during or after step (2).

7. The process of claim 4 wherein the reactants are selected from $C_{1-12}$ monoalcohols, phosphorus sulfides, and antimony oxides or hydroxides.

8. The process of claim 4 wherein the reactants are n-propyl alcohol, diphosphorus pentasulfide, and antimony oxide.

9. The process of claim 6 wherein the reactants are n-propyl alcohol, diphosphorus pentasulfide, and antimony oxide.

* * * * *